United States Patent [19]

Bilhorn et al.

[11] Patent Number: 5,696,591
[45] Date of Patent: Dec. 9, 1997

[54] APPARATUS AND METHOD FOR DETECTING LONGITUDINALLY ORIENTED FLAWS IN A MOVING WEB

[75] Inventors: Robert B. Bilhorn, Webster; Paul Jacques Guiguizian, Pittsford, both of N.Y.

[73] Assignee: Eastman Kodak Company, Rochester, N.Y.

[21] Appl. No.: 583,345

[22] Filed: Jan. 5, 1996

[51] Int. Cl.⁶ .................. G01N 21/84; G01N 21/00; H04N 7/18; H04N 9/47
[52] U.S. Cl. .................. 356/429; 356/430; 356/238; 250/559.03; 250/559.05; 250/559.46; 348/88
[58] Field of Search .................. 356/429–431, 356/238; 250/559.03, 559.05, 559.08, 559.46; 348/88; 382/111

[56] References Cited

U.S. PATENT DOCUMENTS

| | | | |
|---|---|---|---|
| 3,618,063 | 11/1971 | Johnson . | |
| 3,877,821 | 4/1975 | Price et al. | 356/239 |
| 3,972,624 | 8/1976 | Klein et al. | 356/237 |
| 4,247,204 | 1/1981 | Merlen et al. | 356/431 |
| 4,492,477 | 1/1985 | Leser | 356/239 |
| 4,724,481 | 2/1988 | Nishioka | 356/237 |
| 4,724,482 | 2/1988 | Duvent . | |
| 4,896,211 | 1/1990 | Hunt . | |
| 4,922,337 | 5/1990 | Hunt et al. . | |
| 4,982,105 | 1/1991 | Takahashi | 356/431 |
| 5,040,057 | 8/1991 | Gilblom et al. . | |
| 5,068,799 | 11/1991 | Jarrett | 356/430 |
| 5,118,195 | 6/1992 | Dobbie | 356/430 |
| 5,173,748 | 12/1992 | Bilhorn | 356/328 |
| 5,239,184 | 8/1993 | Mancosu et al. | 356/430 |
| 5,426,509 | 6/1995 | Pepliuski | 356/430 |
| 5,434,629 | 7/1995 | Pearson et al. | 348/88 |
| 5,440,648 | 8/1995 | Roberts et al. | 356/430 |
| 5,452,079 | 9/1995 | Okugawa | 356/237 |

*Primary Examiner*—Frank G. Font
*Assistant Examiner*—Jason D. Vierra Eisenberg
*Attorney, Agent, or Firm*—Susan L. Parulski

[57] ABSTRACT

An optical inspection apparatus detects faults in a material coated on a moving web. Multiple cameras are positioned in an array across the width of the web transverse to the direction of the moving web. Each camera comprises a electronic camera and digital signal processor. An illumination source is preferably positioned to illuminate one side of the web. The camera array is positioned on the opposite side of the web aligned with the illumination source. The cameras in the array image the moving web along colas and collect image data from the web. The image is digitized and processed in real-time by averaging each column of image data to produce a profile of light intensity transmitted across the web width from which faults occurring in the longitudinal direction are detected in a host computer.

17 Claims, 2 Drawing Sheets

APPARATUS AND METHOD FOR DETECTING LONGITUDINALLY ORIENTED FLAWS IN A MOVING WEB

FIELD OF THE INVENTION

The present invention relates to an apparatus and method for monitoring uniformity and detecting defects in the surface of a moving web, and specifically in a layered material on a web. The material may be a coating applied to the web surface in a continuous moving web process.

BACKGROUND OF THE INVENTION

The simultaneous application of multiple, thin layers of material with precisely controlled thickness (uniformity) is important for the production of various web and sheet materials, such as photographic film. Defects, such as longitudinal lines or streaks in the finished film, can result from lack of uniformity of the deposited layers on the web in a lateral direction across the width of the web. Such defects are especially disadvantageous in the web coating of photosensitive material, such as photographic film manufacturing, and can contribute to a significant amount of waste because of the large area of the web that can be affected by even a single defect occurrence.

Currently employed methods of detecting longitudinal defects which extend in the direction in which the web travels are either slow or are not capable of reliably detecting the total number of defects. The most reliable method of defect or flaw detection does not take place in real-time while coating occurs, but only after the film has been coated and dried. Samples of the web are cut, exposed to light, photographically processed, and then examined. Because the manufacturing process is continuous, a significant volume of defective material can be produced before the flaw is detected. Real-time web inspection systems have been attempted, but have problems.

In one type of real-time web inspection system, raster scanned light or laser beams are used to detect defects. In this type of system, a beam of light is scanned across all or part of the width of the web at a high speed using a rotating polygonal mirror and the transmitted, reflected, or both portions of the light beam are detected and analyzed to identify defects. Although a few defects are detected, this type of system is relatively insensitive to the majority of lines and streaks that may occur in simultaneous multilayer coatings. U.S. Pat. Nos. 4,982,105, 4,247,204 and 3,972,624 disclose systems which practice the raster scanned light beam approach.

In another type of real time system, a single electronic camera or an array of electronic cameras of the line-scan, area-scan, or time delay and integrate (TDI) type are used to inspect moving web and sheet materials. U.S. Pat. Nos. 5,068,799, 4,896,211, and 4,922,337 disclose systems which uses line scan, area scan, or TDI cameras. This type of system provides greater sensitivity to widthwise coverage variations in multi-layer coatings, such as lines or streaks, then the raster scanned light beam approach system previously described because of the illumination geometry enhancements that are possible with line scan, area scan, or TDI cameras. However, even though the sensitivity of this type of system is enhanced over the raster scan type system, there still are problems.

Real time systems, such as those described above which use a single electronic camera or an array of electronic cameras, can be slow, complex and costly. For example, these systems would first store the image data either in a signal buffer memory or a buffer memory associated with each camera before processing by a single processor or processor associated with each camera. Accordingly, a substantial amount of buffer memory may be required and the processing time can be slow.

PROBLEM TO BE SOLVED BY THE INVENTION

To provide a system for detecting flaws appearing in a moving web which operates in near real time, is simple, is inexpensive and is reliable. Additionally, to provide a system which reduces memory and processor requirements of existing systems.

SUMMARY OF THE INVENTION

According to the present invention, an apparatus and method are provided for detecting flaws appearing in a moving web and especially defects extending longitudinally along the web. Multiple camera modules are positioned in an array across the width of the web transverse to the direction of the moving web to image line scans of the surface and scan adjacent columns of the web. Each camera module comprises a camera and an integrated digital signal processor (DSP) controller. The camera modules are connected to a communications line. An optional illumination source is preferably positioned on a side of the web, opposite to the camera array and aligned with the cameras in the array. The cameras in the array collect image data from the web surface in real-time along each column. The image data is processed by the programmed DSP controller continuously and in real-time by averaging each column of image data to produce a profile of light intensity transmitted through the web across its width. The averaged image data is transmitted along the communications line and is then further processed by a programmed host computer to determine in near real-time when a fault has occurred.

ADVANTAGEOUS EFFECTS OF THE INVENTION

With the present invention, a system which operates in near real-time and is able to reliably detect flaws in a web is disclosed. The cameras and camera controllers in the system process the image data in real time rather than storing the image data which reduces memory requirements and increases the speed of the system. Averaging the image data also improves the signal to noise ratio making detection of flaws easier.

DETAILED DESCRIPTION OF THE INVENTION

Figure 1:
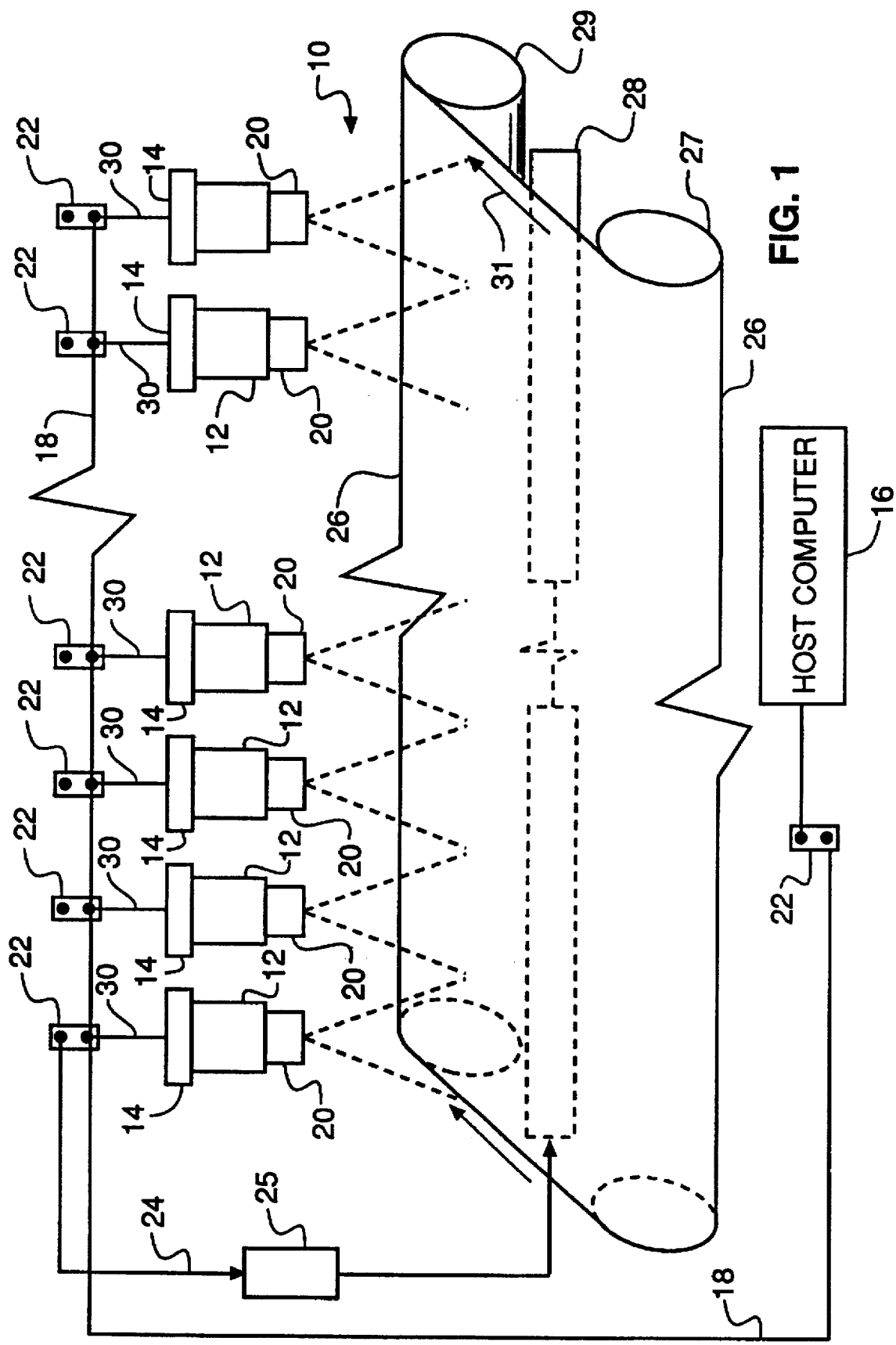
FIG. 1 is a block diagram of a web flaw detection system in accordance with the present invention.

Referring to FIG. 1, a web flaw detection system 10 in accordance with the present invention is shown. System 10 includes an array of digital signal processor (DSP) based camera controllers 14 and cameras 12 which are focused via lenses 20 on a moving web 26. The array of camera controllers 14 and cameras 12 is linear, along a line perpendicular to the direction of travel of the web 26, between reels 27 and 29 in the direction of arrow 31. An optional illumination source 28 is used on the backside of the web to provide transmitted light. With the present invention, a system is disclosed which operates in near real time and is simpler and less expensive than prior web flaw detection systems.

Referring more specifically to FIG. 1, each camera 12 is a CCD camera with a line or two-dimensional CCD element array, which by way of example may be 2048 elements in the cross web direction and 96 elements in the down-web direction. Although CCD cameras 12 are shown, other types of cameras could be used if desired. Each camera 12 is positioned to scan an image of a column of moving web 26 and has sufficient resolution to detect the smallest desired continuous longitudinal imperfection, or streak. Each lens 20 focuses the image of web 26 onto each camera's CCD array. In this particular embodiment, the captured image is digitized by camera 12 and then is sent to DSP based camera controller 14. However, a separate digitizer in the controller 14 or in a separate device (not shown) between camera 12 and DSP-based camera controller 14 may be used, allowing camera 12 to output analog signals, rather than digital data. The number of cameras 12 depends on the width of the web and the field of view of each camera 12. Each camera controller 14 is coupled to a communications line 18. Junctions boxes 22 couple DSP-based camera controllers 14 to communications lines 18 and links 24 and enable cameras 12 and DSP-based camera controllers 14 to be easily added and removed and for breaking out the two serial communications lines.

Each camera 12 has a dynamic range (grey scale resolution) necessary to detect streaks and/or layer nonuniformity in web 26. Preferably, a grey scale resolution of ten bits or more per pixel is used. Cameras 12 may require special cooling devices (not shown) to provide the required dynamic range. A camera 12, such as that available from Dalsa, Inc., Ontario Canada, CLF22048 with an S244 10 bit A/D option, could be used.

Any line scan camera, time delay integration (TDI) camera, or area scan camera which produces a stream of analog or digitally encoded intensity values can be used. The rate of the data stream should not exceed the speed capabilities of DSP controller 14. Therefore, in one preferred embodiment, an array of digital CCD cameras having 96 rows, each made up of 2048 pixels digitized to a precision of 10 bits at a rate of 1 MHz, is used. Camera 12 requires, as inputs, several DC voltage levels which are provided by a power supply (not shown in the figures), and a TTL clock which is divided by four internally to provide a pixel rate clock. Camera 12 produces as outputs in addition to the digital pixel data, a pixel clock and a line clock.

One DSP based camera controller 14 with associated support circuitry is used with each camera 12. Preferably, DSP based camera controllers 14 are coupled to ten or more bit per pixel CCD cameras 12, although they are compatible with any type of analog or digital camera 12 whose output does not exceed the input speed capabilities of DSP-based camera controller 14. Each DSP-based camera controller 14 contains local program memory and is also supported with sufficient memory for intermediate and final result storage, as would be readily understood by one skilled in the field. Each DSP based camera controller 14 provides signals required for operation of the camera 12 including timing signals and receives image data from camera 12. Each DSP based camera controller 14 also processes the image data in real-time by averaging each column of the image data to produce a profile of the reflected or transmitted light intensity across the width of the web. Averaging can be performed either over groups of rows in a batch sense, or in a continuous moving average mode. The unaveraged image data itself is not stored at DSP based camera controller 14, reducing memory capacity requirements (e.g. buffer memory) and commensurate costs, as well as board size.

The averaged data from each DSP based camera controller 14 is transmitted over a shared high speed serial communications link 18 to host computer system 16. An industry standard protocol, such as RS485, is used for communications on high speed serial communications bus 18. Each DSP-based camera controller 14 and camera 12 combination has a unique I.D. number or address assigned to it for identification purposes. This is used to identify the physical location of camera 12 on the line across the web width to host computer 16 so that commands may be sent to DSP-based camera controllers 14 individually, so that results sent from DSP-based camera controllers 14 to computer 16 can be correlated with precise process locations. In a preferred embodiment, DSP-based camera controllers 14 plug directly into connectors (not shown) provided on the back of a commercially available CCD based digital electronic cameras 12, reducing wiring to improve reliability.

Each DSP-based camera controller 14 is capable of controlling an illumination source 28 through a second serial interface, communication line 24. Illumination source 28 is controlled in a closed loop system and uses pixel intensity values derived from the image data captured by camera 12 to adjust the intensity of illumination source 28. Unlike the shared serial communications bus 18 used for communication with host computer 16, in a preferred embodiment the illumination controller 25 uses a direct serial link 24 from one DSP-based camera controller 14 to one illumination controller 25. In a multiple camera installation, each illumination controller 25 could control an individual illumination source 28 or a single illumination controller 25 could control an illumination source 28 used by multiple cameras 12.

Host computer 16 is used to send commands and receive data to and from each DSP-based camera controllers 14. Host computer 16 is interfaced to the high speed communications line 18. One host computer 16 can be used to control multiple networks of DSP-based camera controllers 14, for example for flaw detection on several webs.

Camera 12 is positioned to scan the material as it moves past its field of view while the material is being illuminated from above or beneath the web by optional illumination source 28. Light passing through web 26 will be distorted by any streaks or layer nonuniformity present on web 26. In this particular embodiment, illumination source 28 is a lamp, such as an incandescent lamp, a fluorescent lamp, an array of LEDs, or laser diodes, which is aligned with camera 12.

Illumination source 28 may be any wavelength of light and therefore may operate in the visible light spectrum, but may also emit light in the x-ray, ultra-violet, or infrared wavelength ranges. Camera 12 must be compatible with the light wavelength selected and being emitted from illumination source 28. Additionally, illumination source 28 may consist of a particle beam such as electrons or ions. Inspection could also take place without illumination source 28, such as in thermal infrared imaging, where the object (i.e. the web 26) itself acts as the source. For sensing the uniformity of photographic film being produced on a moving web according to the method of the present invention, near and mid infrared wavelengths are preferred, with about 1000 nm being the wavelength particularly preferred for the inspection of light sensitive material, such as a photographic film.

DSP-based camera controller 14 controls illumination source 28 by sending commands over a standard serial communications line 24 to an illumination controller 25. Illumination source controller 25 sets the light intensity in response to commands from each camera controller 14. Although not shown, separate illumination sources 28 could be used for and aligned with each camera 12 and each DSP based camera controller 14 could control its own illumination source 28. The light level for each illumination source 28 should be set to provide full use of the dynamic range of camera 12.

Figure 2:
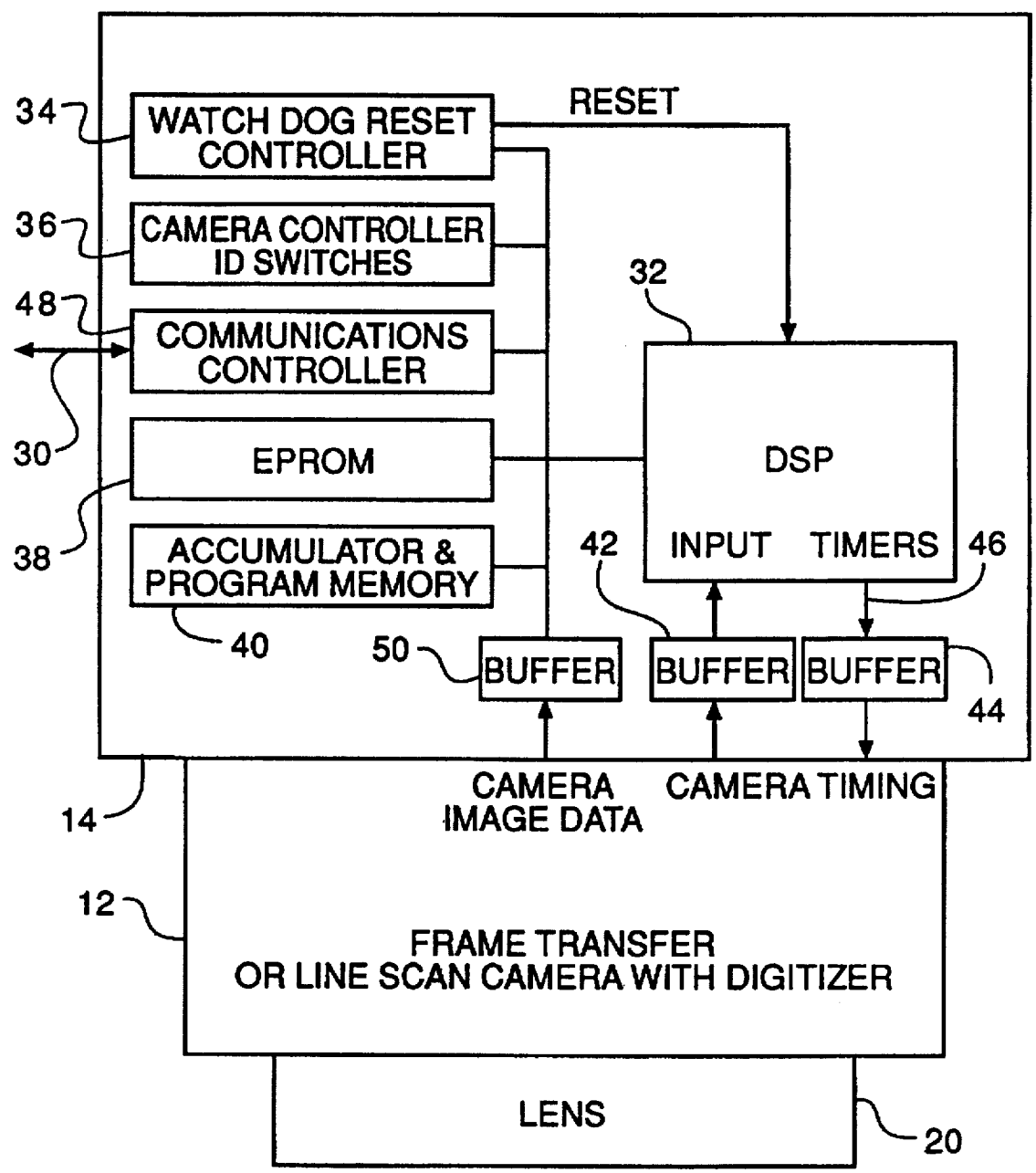
FIG. 2 is a block diagram of a DSP camera controller, a camera and lens used in FIG. 1.

Referring to FIG. 2, DSP based camera controller 14 contains a DSP chip 32 such as the TMS320C31 available from Texas Instruments, Dallas, Tex., U.S.A., which comprises a computer with timers, interrupts and input and output (I/O) capabilities. With DSP chip 32, such as the TMS320C31, data comprised of 2048 two byte pixels per line at a line rate in excess of 500 lines per second can be processed.

Camera controller ID 36 is used by host computer 16 to distinguish between camera controllers 14. In this particular embodiment, the ID is set with a two position hex switch allowing 255 unique addresses. All commands sent by host computer 16 would be preceded by the DSP based camera controller address identifying the specific camera controller 14 to which the command was being sent. In addition, all camera controllers 14 would respond to commands preceded by an address of zero to allow commands to be sent to all camera controllers 14 simultaneously.

In a preferred embodiment, a serial communications controller 48 on DSP-based camera controller 14 has two channels. One channel 30 is used for the high speed serial network 18 connecting the host computer 16 to DSP-based camera controller 14. The other channel 24 is used to communicate with illumination controller 25. The communications controller 48 may be a chip, such as the Z8523016VSC available from Zilog, Dallas, Tex., U.S.A.

To operate the system 10 (with reference to FIGS. 1 and 2), first a signal is sent from host computer 16 to all DSP-based camera controllers 14, over the shared high speed serial communications line (a bus) 18, commanding camera controllers 14 to initialize. As part of initialization, each DSP-based camera controller 14 sets up timers 46 for camera image data transfer to DSP-based camera controllers 14. The timer data is buffered in buffers 44. Separate timers (not shown) control the pixel data transfer rate to the DSP-based camera controller 14, and the image data line rate in lines per second. Unlike prior systems, the image data line rate does need not to match the speed of the moving web (i.e. not synchronous).

DSP-based camera controller 14 also performs a power-on initialization by reading the program stored in EPROM 38 (or any other nonvolatile memory). Initialization includes reading controller ID 36, setting up communications controller 48 for later communications with host computer 16 and illumination controller 25, and enabling watch dog reset timer 34. Watch dog timer 34 is set up to reset and restart DSP-based camera controller 14 if a program fault is detected or if host computer 16 requests a reset. The DSP-based camera controller program must periodically reset watch dog timer 34 to prevent it from resetting DSP chip 32. A program fault would prevent the periodic reset causing the watch dog timer to reset DSP chip 32. A reset has the same effect as a power-on initialization.

Next a command is sent from host computer 16 to all DSP-based camera controllers 14 over bus 18 to start image data collection. Each DSP-based camera controller 14 clears a local accumulator memory 40 for image data storage. Each camera 12, along with its control and digitizing circuits, converts the imaged light into a line of digital data representing the intensity of the transmitted light over the field of view of each camera 12. In this particular embodiment, each camera 12 produces 2048, 16 bit pieces of data per line. Camera 12 sends timing signals to DSP-based camera controller 14 through a buffer 42, to indicate when a line of image data is being transferred out of camera 12. The digital data is sent to DSP-based camera controller 14 through a buffer 50. Image data buffer 50 may also store a part of or the entire line of image data to synchronize the timing of DSP chip 32 with the camera timing. The image data is added to a local accumulator storage array 40 in DSP-based camera controller 14. After accumulating the number of image data lines specified by host computer 16, DSP-based camera controller 14 then computes statistics, such as mean or standard deviation and waits for communication from host computer 16. The output data from each DSP-based camera controller 14 is referred to herein as average data and the statistics operation is referred to as averaging. The term "averaging" should, therefore, be taken to mean any statistical process which obtains the base of image data, underlying the mean and standard deviation. One example of averaging is disclosed in U.S. Pat. No. 3,972,624 to Klein et at, which is herein incorporated by reference.

Host computer 16 then commands each DSP based camera controller 14 to transfer the accumulated average data to the host computer. Host computer 16 will then examine the average data from each DSP-based camera controller 14 for conditions which indicate an error or defect in the web, known as "out-of-spec" conditions. Examination of each image data segment by host computer 16 comprises comparing the average data from each DSP based camera controller 14 to expected results. Average data which is more than a fixed percentage or standard deviation away from expected results will be identified as an error or defect in the web. In conducting this analysis, host computer 16 takes into account the fact that image data of a defect free sample will contain variations due to the particular type of camera 12 used and the lighting conditions which do not indicate defects in the web. The process of removing this expected variation is well known to those skilled in the art and is called flat field correction. The flat field correction may also be performed by DSP-based camera controller 14 before the average data is sent to host computer 16.

The present invention simplifies the complexity of known inspection systems and is a highly modular system which can be designed and customized, as would be apparent to one skilled in the inspection field, to provide a common solution for a variety of installations (e.g. from pilot coating facilities to single and multiple pass production operations). The use of DSP based camera controller 14 with a digital signal processor (DSP), located at each camera 12, advantageously provides real-time processing of the image data to produce a coating density profile across the width of the web without the need for large buffer memories and while simultaneously reducing the system cost and complexity because of the reduced memory and processing requirements. Widthwise uniformity evaluation and line and streak detection are performed by averaging columns of image data to produce a profile of the coating density across the web. This is possible since the imperfections are often continuous in the longitudinal direction. The present invention eliminates the need to strobe or synchronize the acquisition of the images with the line speed in order to stop motion. Further, continuous real-time inspection and longitudinal flaw detection is enabled without the need of a frame buffer.

Numerous advantages are realized in using system 10 as compared with competing frame buffer based image processing systems which have greater complexity and cost. Significant performance advantages are realized over prior approaches by allowing for continuous operation and fault determination in near real-time; whereas frame based processing is limited by the amount of memory contained in the system and may not provide results as quickly.

A number of other features embodied in system 10 are also advantageous. For example, elimination of the cabling between the cameras 12 and controllers 14 reduces cost, complexity, physical size of the installation, and increases reliability and decreases susceptibility to electrical noise. The ability to control illumination intensity is built into each DSP-based camera controller 14 so all controllers 14 are identical and can be simply placed in series across the web width. This may be required if each camera 12 is used with a dedicated illumination source 28. The use of simple high speed serial communications in system 10 provides a low cost, easily installed and maintained, highly flexible system. By performing the majority of the data reduction in controller 14, the bus bandwidth requirements are not great; connections are made easily, and reconfiguration is possible with minimal effort. In addition, all of cameras 12 and DSP-based camera controllers 14 can be identical. The software program run by the DSP-based camera controller 14 is the same regardless of the installation, and the software on host computer 16 need only take into account the number of cameras 12 and DSP-based camera controllers 14 on the bus.

The method and apparatus of the present invention may be used to evaluate, in real-time, the entire field of the web material, or discrete sections of the web material. Edges of web materials such as photographic films may not be uniform due to material flow dynamics with respect to thickness as compared with the rest of the web material. Often, edges of the material must be trimmed from the finished product as waste. It is important, therefore, to restrict the amount of waste to be trimmed. Cameras 12 of the present invention could be placed at the edges, for example focusing on the outside 1–5 cm. of the film, to determine the uniformity of the film near the edges, and determine where the trim cut must be made to assure quality of the finished film. Similarly, the edge of the liquid coating could be located relative to the edge of the support material and this information fed back to a web steering mechanism.

Many other modifications and variations of the present invention are possible to the skilled practitioner in the field in light of the teachings herein.

PARTS LIST

12—camera
14—controller
16—host computer
18—high speed serial communications line (between controllers and host computer)
20—lens
22—junction box
24—serial communications link (to illumination controller)
25—illumination controller
26—moving web
27—reel, supply
28—illumination source
29—reel, take-up
30—4 conductor (RJ11) communications controller connection
31—arrow indicating direction of web travel
32—DSP chip
34—watch dog timer
36—controller ID, switch bank for setting
38—eprom (memory)
40—accumulator and program memory
42—buffer, timing data from camera
44—buffer, commands to camera
46—timing signals from timers in DSP
48—communications controller
50—buffer, image data from camera

We claim:

1. A method for detecting longitudinally oriented flaws in a moving web having a width, comprising:

transporting the web in a first direction at a predetermined rate of motion;

positioning an array of cameras across the web width, transverse to the first direction of the moving web;

imaging adjacent columns of a surface of the web on a first side thereof, at a continuously adjustable non-synchronized rate relative to the rate of motion of the web;

collecting image data corresponding to said columns imaged by said cameras;

processing the image data in real-time by averaging columns of image data, to produce a width-wise profile across the full web width;

transmitting said averaged image data to a processing unit; and detecting longitudinally oriented flaws from said averaged image data.

2. The method of claim 1 further comprising the step of positioning an illumination source to illuminate said first side of said web.

3. The method of claim 2 wherein said illumination source emits charge particles, and the cameras detect said charged particles emitted by said illumination source.

4. The method of claim 2 wherein the illumination source emits wavelengths of light in the range selected from the group consisting of: infrared, x-ray, ultra-violet and visible light.

5. The method of claim 1 further comprising a step of positioning an illumination source on a second side of said web opposite said first side.

6. The method of claim 1 further comprising the step of serially communicating said data from said cameras to a computer using a serial communications line.

7. The method of claim 1 further comprising the step of controlling said cameras and the processing of said data from said computer.

8. The method of claim 7 wherein said controlling is carried out by addressing the cameras.

9. The method of claim 1 wherein the data averaging is performed upon successive groups of digital data corresponding to images from each of said cameras as said web moves in the longitudinal direction of the moving web.

10. The method of claim 9 wherein said averaging produces averages that are updated continuously by adding and replacing digital data to form each of said groups.

11. The method of claim 1 wherein said processing step is carried out to detect uniformity at the edges of said web.

12. The method of claim 1 wherein the averaging is performed over groups of data representing linear images in the longitudinal direction of the moving web material and as carried out in a continuous moving average mode.

13. The method of claim 1 further comprising providing at least part of said real-time processing to image data in a host computer.

14. The method of claim 1 further comprising the step of connecting an array of cameras together to said host computer using a serial communications line.

15. The method of claim 1 wherein said columns include the edge of said web whereby coating thickness near the edge of the moving web is monitored continuously.

16. A method for detecting longitudinally oriented flaws in a moving web having a width, comprising:

transporting the web in a first direction at a pre-determined rate of motion;

positioning an array of cameras across the web width, transverse to the direction of the moving web;

determining a light operation level for said cameras;

determining an imaging rate in response to said light operation level;

imaging adjacent columns of a surface of the web on a first side thereof, at a continuously adjustable non-synchronized rate relative to the rate of motion of the web;

collecting image data corresponding to said columns imaged by said cameras;

processing the image data in real-time by averaging columns of image data, to produce a width-wise profile across the full web width;

transmitting said averaged image data to a processing unit; and detecting flaws from said averaged image data.

17. An optical inspection apparatus for detecting longitudinally oriented flaws in a web moving in a first direction at a pre-determined rate of motion, comprising:

an array of cameras spaced from the web and directed toward a first surface of the web, said array extending across the width of the web such that a complete field of view of the web is achieved across adjacent columns of said web, each camera including an digital signal processor controller for collecting and continuously averaging image data from the surface of the web in real-time by averaging data columns from the image data to produce a width-wise profile of light intensity transmitted across the web width; and a continuously adjustable controller controlling the rate at which the image data is collected such that the rate is non-synchronous relative to the pre-determined rate of motion of the web.

* * * * *